United States Patent
Warmuth

(10) Patent No.: US 7,548,777 B2
(45) Date of Patent: Jun. 16, 2009

(54) COMPUTERIZED METHOD FOR PREDICTING THE DIASTOLIC REST PERIOD IN A CARDIAC CYCLE

(75) Inventor: Carsten Warmuth, Berlin (DE)

(73) Assignee: Siemens Aktiengesellschaft, Munich (DE)

( * ) Notice: Subject to any disclaimer, the term of this patent is extended or adjusted under 35 U.S.C. 154(b) by 448 days.

(21) Appl. No.: 11/378,561

(22) Filed: Mar. 17, 2006

(65) Prior Publication Data

US 2006/0241511 A1    Oct. 26, 2006

(30) Foreign Application Priority Data

Mar. 17, 2005   (DE) ................ 10 2005 012 386

(51) Int. Cl.
*A61B 5/04* (2006.01)
(52) U.S. Cl. .................. 600/513; 600/509; 600/534
(58) Field of Classification Search ................. 600/513, 600/521, 411, 534; 607/20, 23, 25
See application file for complete search history.

(56) References Cited

U.S. PATENT DOCUMENTS 4,930,508 A * 6/1990 Shimoni et al. ............ 600/410
2003/0174804 A1   9/2003 Bulkes et al.

FOREIGN PATENT DOCUMENTS

WO    WO 02/43587    6/2002

OTHER PUBLICATIONS

Shecter G, et al. Rest period duration of the coronary arteries: Implications for magnetic resonance coronary angiography, Jan. 3, 2005, Medical Physics 32(1), pp. 255-262.*
"Analysis of the Heart Rate and Its Variation Affecting Image Quality and Optimized Reconstruction Window in Retrospective ECG-Gated Coronary Angiography Using Multidetector Row CT," Lee et al, IEEE Trans. on Nuclear Science, vol. 51, No. 1 (Feb. 2004), pp. 225-231.
"Prediction of Heart Rate Variation During Coronary MRA, Using a Neuronal Network," Buerhrer et al, Proc. Intl. Soc. Mag. Reson. Med. 11 (2004), p. 1885.

* cited by examiner

*Primary Examiner*—Carl H Layno
*Assistant Examiner*—Brian T Gedeon
(74) *Attorney, Agent, or Firm*—Schiff Hardin LLP

(57) ABSTRACT

In a method to predict the diastolic rest period in the cardiac cycle of a patient under examination, the linear relation between heart rate and position of the diastolic rest period in the cardiac cycle is determined by determining the position of the diastolic rest period in at least two different heart rates of the examined patient, determining the breathing motion using rate and/or acceleration sensors and predicting the next diastolic rest period under consideration of the breathing motion and the definite relation between the heart rate and the position of the diastolic rest period of the patient under examination.

15 Claims, 3 Drawing Sheets

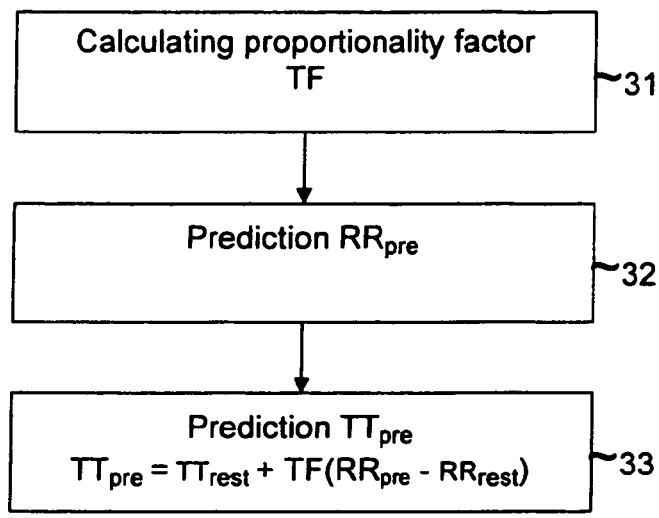
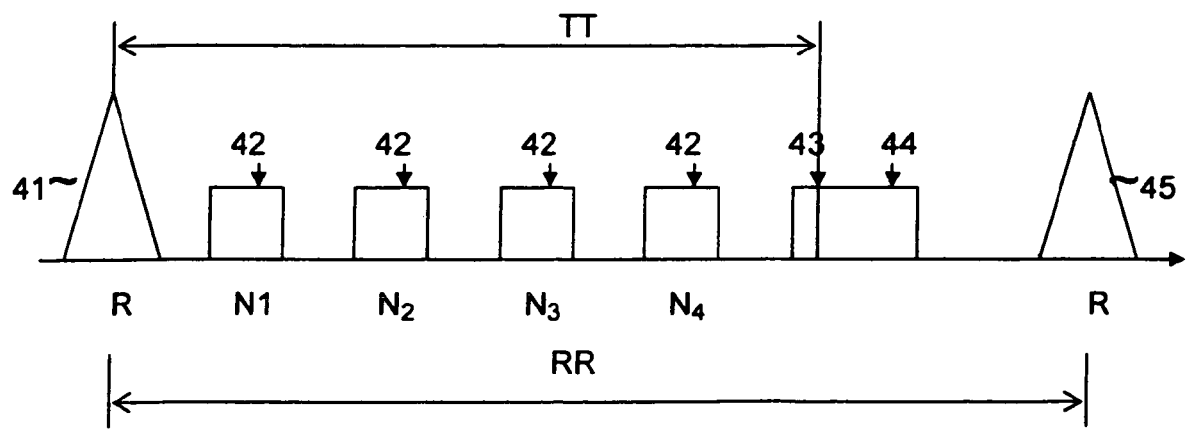

COMPUTERIZED METHOD FOR PREDICTING THE DIASTOLIC REST PERIOD IN A CARDIAC CYCLE

BACKGROUND OF THE INVENTION

1. Field of the Invention

The present invention at hand involves a computerized method to predict the diastolic rest period in the cardiac cycle as well as a method to depict the coronary arteries by means of magnetic resonance imaging. The diastolic rest period is predicted in order to use it later for diagnostic imaging.

2. Description of the Prior Art

Angiographic examinations of the coronary arteries are made by using x-ray equipment to depict the coronary arteries in order to detect constrictions in the coronary arteries. By means of magnetic resonance imaging, it has recently also been possible to produce images of the course of the coronary arteries. However, these so-called MR angiographies of the coronary arteries, however, may require a measuring (data acquisition) period of up to 30 minutes.

To record MR images of the heart, the rest period of the heart at the end of the diastole is used in order to depict the coronary arteries of the heart. At the same time, the ECG signal of the examined patient is used to record the MR images in order to determine the position of the diastolic rest period of the examined patient so that the MR images can be recorded during this rest period. The period for recording MR images in the rest period of the heart in the diastole is between 50 and 200 ms. In this period, the image data for the MR angiography is acquired, whereby in this case segmented recording procedures are used in which one part of the total data required for a complete data record is recorded with each diastole of the cardiac cycle.

One of the problems that occur with these MR angiographies is that it is necessary to predict the position of the diastolic rest period of the examined patient during the measuring period in order to record the MR images during this period of the diastole. The heart rate can change during the examination period so that through the changing heart rate the position of the diastole also changes. If a constant heart rate is assumed and it is assumed that the diastole occurs at a fixed point in time, it can occur that, through the change of the rest period during image recording, the rest point of the diastole has not yet occurred or is already over. This has a negative effect of the image quality.

From DE 28 13 830 A1, a device is known that makes heart images by means of cathode beam scanning which determines the position of the diastole for diagnostic imaging.

From Lee S. H. et al. "Analysis of the Heart Rate and its Variation Affecting Image Quality and Optimized Reconstruction Window in Retrospective ECG-Gated Coronary Angiography Using Multidetector Row CT" in IEEE Transactions on Nuclear Science, Vo. 51, No. 1, February 2004, pp. 225-230 it is known how the heart rate of patients changes during computer tomography imaging of the heart.

From US 2003/0174804 A1 a procedure for diagnostic imaging of the heart by means of computer tomography is known in which, by means of the ECG and by means of the mechanical movement of the cardiac region, the period in which to measure the heart is determined.

In "Prediction of Heart Rate Variation during Coronary MRA Using a Neuronal Network," in Proc. ISMRM 11 (2004), p. 1885, M. Buehrer et al. tried to determine the heart rate by means of neuronal networks in order to improve the imaging quality of the magnetic resonance angiography of the coronary arteries. However, the use of a neuronal network, however, is quite complex.

SUMMARY OF THE INVENTION

An object of the present invention is to improve the prediction of the variation of the heart rate and especially the position of the diastolic rest period of the cardiac cycle. By improving the prediction of the cardiac cycle, it is intended to improve coronary angiography.

This object is achieved in accordance with the present invention by a computerized method that predicts the diastolic rest period in the cardiac cycle of an examined patient wherein, as a first step, the linear relation between the heart rate and the position of the diastolic rest period in the cardiac cycle is automatically electronically determined by determining the position of the diastolic rest period in at least two different heart rates of the examined patient. By assuming a linear relation between a change of the cardiac cycle and the position of the diastolic rest period it is possible to establish, by means of determining the position of the diastolic rest period during two heart rates, how the position of the rest period changes when the heart rate changes. As a representation of a second step, the breathing motion is obtained and the breathing motion automatically electronically is determined therefrom. The cardiac cycle or heart rate is also dependent on the breathing motion of the examined patient. By determining the breathing motion, under consideration of the signals from the rate or acceleration sensors, precise positioning can be made regarding the breathing motion, which generally improves the prediction of the position of the diastolic rest period in the cardiac cycle. Subsequently, the next diastolic rest period is automatically electronically predicted under consideration of the breathing motion and the definite linear relation between heart rate and position of diastolic rest period for this particular patient under examination. By determining precisely the breathing motion and by determining the relation between heart rate and position of the diastolic rest period, it is quite easy to predict the position of the diastole in the cardiac cycle for the examined patient.

In a preferred embodiment, the determination of the linear relation as well as the determination of the breathing motion is performed by means of magnetic resonance imaging (MRI). If the rest period of the heart during the diastole can be predicted well, it is also possible with magnetic resonance imaging to get a better picture of the coronary arteries, because it is largely avoided that the signal reception for the images occurs at a point in which the heart is not in the diastolic rest period.

The representation of the breathing motion can be acquired as a signal from a sensor, such as a sensor that detects movement of the diaphragm of the subject. Rate sensors or acceleration sensors are suitable for this purpose.

In a preferred embodiment, however, an MR measurement (scan) with several magnetic resonance images for various heart rates is made in order to determine the linear relation between heart rate and position of the diastolic rest period. By recording several MR images in short timed distances during a cardiac cycle, it is possible to determine the position of the diastolic rest period by examining the chronological sequence of the pictures (as in a movie). In this case, the position of the diastolic rest period is determined for two different heart rates. These rates can be, for instance, the rates of the heart during the rest period, as well as an increased heart rate resulting from hyperventilation of the examined patient. For these two different heart rates, the cardiac cycle is recorded by means of several MR images in chronological sequence, and for both rates, the position of the diastolic rest period in the cardiac cycle is determined. Of course, the heart rate is not only changed through hyperventilation of the examined patient. This change of the heart rate can also have other causes, such as medication or physical exertion.

Preferably, the breathing motion of the examined patient is determined by detecting the position and movement of the diaphragm. It is also known that the breathing motion has an effect on the cardiac cycle. A good indicator for the determination of respiration is the determination of the position of the diaphragm in the examined patient. In order to make good predictions about the movement of the diaphragm, preferably several determinations of the diaphragm positioning are made during one cardiac cycle. For instance, the position of the diaphragm during one cardiac cycle can be determined by means of nuclear magnetic resonance by taking at least three navigator images, in which, through the position of the diaphragm in at least three navigator images, besides the position itself, also the rate and/or acceleration of the diaphragm can be taken into consideration. As is known to experts in the field of magnetic resonance imaging, it is possible, by means of navigator technology and the additional employment of spin and gradient echoes, to detect in very short recording times positional changes of the measuring object, in this case the diaphragm. With navigator technology the position of the diaphragm is determined in the head-toe direction. By using at least three navigator images during one cardiac cycle, the movement of the diaphragm can be exactly determined and, consequently, this movement can be taken into consideration in the prediction of the cardiac cycle.

Preferably, in determining the linear connection between heart rate and position of the diastole, a proportionality factor TF is determined. This proportionality factor TF indicates the gradient of the curve which is defined by the position of diastolic rest period in the cardiac cycle and the heart rate. Usually, an electrocardiogram (ECG) of the patient is recorded during the examination to determine the heart rate. Then, for a determination of TF, the timed distances of the R-wave (i.e., the R-wave peak) of the ECG to the position of the diastolic rest period TT for two different heart rates can be determined. The quotient from the difference of TT- and the difference of RR in both heart rates results in the proportionality factor TF.

Preferably, in order to predict the position of the diastolic rest period in the cardiac cycle, the timed distance RR from the last R-wave to the next R-wave is predicted in the electrocardiogram. After the prediction of the timed distance RR, a timed distance TT between the last R-wave and the expected diastole can be determined.

Preferably, in order to predict the distance of the two R-waves, the two previous RR intervals are used, as well as the breaching motion, at which the breaching motion is measured through the movement of the diaphragm under consideration of rate and/or acceleration elements.

In a preferred embodiment, a calibration measurement is performed to predict the RR interval, in which the position of the diaphragm is determined by at least three navigator images. The position of the diaphragm and the timed distance of the last two RR intervals can be used to determine the parameters in an optimization algorithm, which are used in a prediction model of the timed distance RR.

By means of the calibration measurement, the coefficients are determined, which determine the quotient of the last two RR intervals and the breathing motion, in order to predict the next RR interval.

If now the RR interval can be predicted, it is possible to determine, by means of the proportionality factor TF and the predicted timed distance RR, the position of the diastolic rest period in the cardiac cycle, that is, the timed distance of the R-wave to the diastole TT. If now the rest position in the diastole TT can be determined, it is possible to acquire, in this rest window of the diastole, MR data for magnetic resonance angiography of the coronary arteries.

DESCRIPTION OF THE DRAWINGS

FIG. 3 is a flowchart of the steps to calculate the position of the diastole after the calculation of TF.
FIG. 4 is a diagram of the image sequence for recording the calibration measurement and the angiography measurement.

DESCRIPTION OF THE PREFERRED EMBODIMENTS

Figure 1:
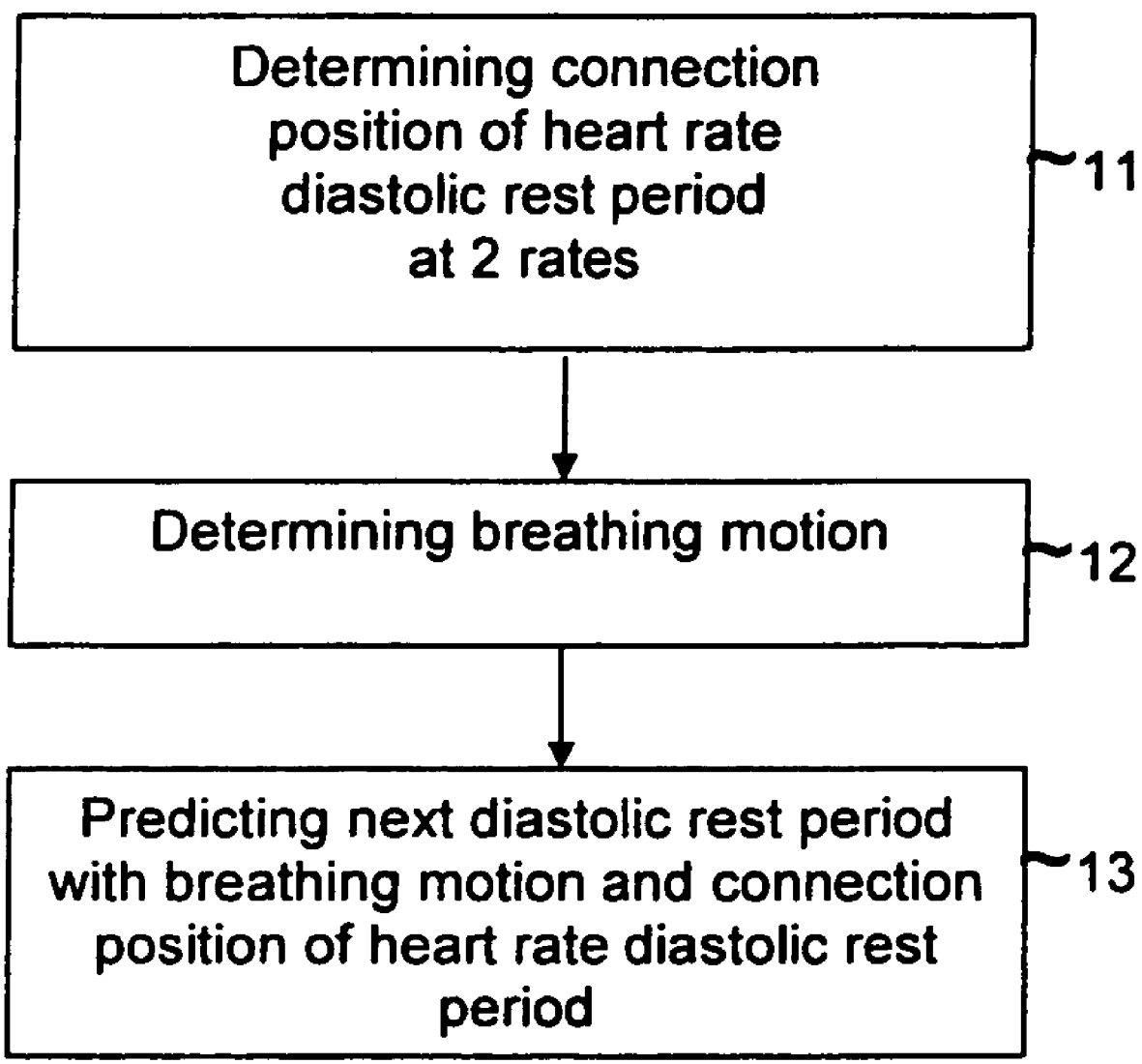
FIG. 1 is a flowchart of the basic steps to determine the position of the diastolic rest period according to the invention.

FIG. 1 depicts a diagram of the basic steps to predict the diastolic rest period in the cardiac cycle. As a first step 11, the connection between the heart rate and the diastolic rest period is determined by determining for two heart rates, for instance, through recording of MR images, in short timed distances, the position of the diastole, in which case the heart rate is known. As a second step, the breathing motion involving rate and/or acceleration elements is determined in order to predict the next cardiac cycle under consideration of the breathing motion and the last two cardiac cycles. For this purpose, the ECG of the examined patient is recorded during the measurements, and from the distance of the last R-wave and the R-wave before last and the breathing motion, the occurrence of the next R-wave is predicted. By taking into consideration the breathing motion and the connection between heart rate and position of the diastole, in step 13, the position of the next diastolic rest period in the cardiac cycle can be predicted.

Figure 2:
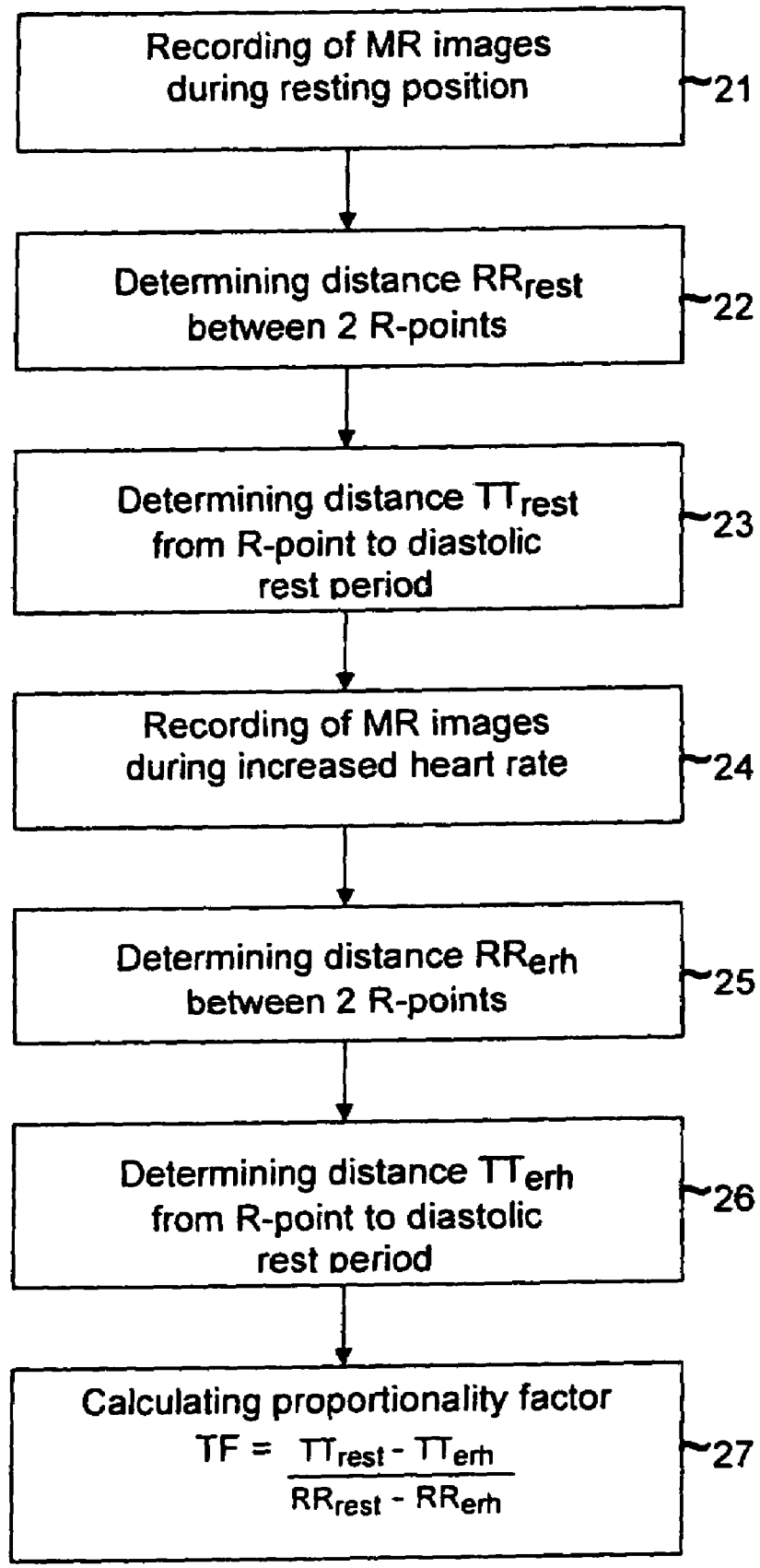
FIG. 2 is a flowchart of the steps to calculate the proportionality factor TF.

FIG. 2 shows in more detail how the relation between the heart rate and the position of the diastolic rest period can be determined in which, in a first approximation, a linear relation between the change of the diastolic rest period and the heart rate is assumed.

In FIG. 2, in a first step 21 with a first heart rate, for instance, the rest rate to determine the position of the diastolic rest period, a series of MR images are recorded in which the time resolution has to be in a way that several pictures are recorded per cardiac cycle sp as top be able to determine precisely the systole and the diastole. At the same time, during the measurement, an ECG of the examined patient is recorded. Then, by means of the ECG, the rest interval $RR_{rest}$ between two R-waves of the ECG can be determined (step 22). Also for the rest rate, the distance from the R-wave to the diastole $TT_{rest}$ for the rest rate of the heart can be determined, that is, the rest position in the end diastole, measured from the R-wave (step 23). Subsequently, the procedure is repeated for a higher heart rate. The increase in heart rate can be caused, for instance, through hyperventilation of the examined patient or through medicinal influences of the heart rate. There could certainly be also other causes for an increase in heart rate. In step 24, just as in step 21, with the increased heart rate, MR images are recorded in short timed distances in order to determine in step 25 the distance of the R-waves $RR_{erh}$ between two R-waves. Also with the increased heart rate, the distance from the R-wave to the diastole $TT_{erh}$ is determined (step 26). Assuming a linear connection between a change in the cardiac cycle and the change of the position of the diastole, a proportionality factor TF can be calculated by means of the parameters determined in steps 22, 23, 25, and 26. This proportionality factor TF shows how the position of the rest window of the diastole in the cardiac cycle changes if the heart rate, that is, the distance of the two R-waves to each other, changes (step 27).

FIG. 3 depicts how, after a calculation of the proportionality factor TF, the distance of the diastolic rest period starting from the R-wave can be determined by means of a prediction of the R-wave.

After in step 31, as desribed in the context of FIG. 2, the proportionality factor TF has been calculated, the distance to the next R-wave is predicted in step 32. This R-wave distance, however, is also dependent on the breathing motion of the patient under examination. Therefore, in predicting RR, the breathing motion, for instance, the movement of the diaphragm, is taken into consideration. The R-wave distance can be approximated, for instance, by means of the following equation:

$$RR_{pre} = P_1 RR_2 + P_2 RR_1 + P_3 N_1 + P_4 N_2 + P_5 N_3 + P_6 N_4 \quad (1)$$

In this equation, $RR_2$ describes the duration of the RR interval before last, $RR_1$, i.e. the last distance between two RR-waves. The values $N_1$ through $N_4$ describe the effect of respiration on the RR interval, in which $N_1$ through $N_4$ are the position values of the diaphragm to a reference position, for instance the endexpiratoric position of the diaphragm, as described in the context of FIG. 4. In a calibration measurement, for instance, a period between 2 and 4 minutes, preferably 3 minutes, the RR distance can be measured and also the position of the diaphragm with the four navigators, so that the coefficients $P_1$ through $P_6$ can be calculated by means of an optimization algorithm, for instance, a least-square-fit-algorithm. The coefficients $P_1$ through $P_6$ indicate to what extent the factor positioned after the coefficients influences the position of the next RR interval $RR_{pre}$ to be predicted.

FIG. 4 shows the sequence of diagnostic imaging that can be used for the following calibration measurement and subsequent MR angiography of the coronary arteries. After a first R-wave 41, four navigator images are recorded. These navigator images serve the purpose of determining the position values $N_1$ through $N_4$ of the diaphragm in the cardiac cycle. By means of the four recorded navigator images, the breathing motion can be determined with rate and/or acceleration elements because the four measuring points of the diaphragm allow for a prediction of position, rate and acceleration of the diaphragm. Subsequently, possible dissection points or sequences 43 follow before the actual diagnostic imaging 44 can be started, in which case at the beginning of angiographic diagnostic imaging 44 the heart should be in the diastolic rest position. Subsequently, after the diagnostic imaging, the next R-wave 45 arrives. As depicted in FIG. 4, RR describes the timed distance between the R-waves 41 and 44. The parameter TT describes the distance from the R-wave until the diastolic rest period at which the actual angiographic diagnostic imaging is performed.

The sequence shown in FIG. 4 can now be used in a first calibration procedure, for instance, over a period of 3 minutes, in order to predict an RR interval from the ECG data, and the data from navigators 1 through 4. The data accumulating during this calibration period can be used to determine the coefficients $P_1$ through $P_6$ of equation 1. As soon as the coefficients $P_1$ through $P_6$ are known, the R-wave distance $RR_{pre}$ can be predicted.

It is not necessarily required to perform this calibration measurement in order to determine the coefficients. It is also possible to determine other starting values $P_1$ through $P_6$, or to take previous measurements and to improve these during the actual angiography recording.

If now, as indicated in step 32 of FIG. 3, the R-wave distance RR has been predicted, the parameter $TT_{pre}$ can be predicted from the prediction of the R-wave distance. Then, this parameter $TT_{pre}$ is used to trigger the angiographic diagnostic imaging, that is, after the $TT_{pre}$ procedure, the actual coronary angiographic diagnostic imaging is started.

As depicted in step 33, the position of the diastolic rest period can be predicted, starting from the R-wave, with the following equation:

$$TT_{pre} = TT_{rest} + TF(RR_{pre} - RR_{rest})$$

By assuming the linear connection and determining the gradient TF, the trigger delay $TT_{pre}$ can be calculated after the parameter $TT_{rest}$ in the heart beat resting position, the coefficient TF, and the R-wave distances $RR_{pre}$–$RR_{rest}$ are known.

For the actual angiographical diagnostic imaging, the sequence depicted in FIG. 4 is used again, in which, for instance, for the angiographical diagnostic imaging 44 a three-dimensional SSFP sequence can be used (staedy state free precision). Before the angiographical diagnostic imaging, for instance, a dissectioning of the magnetization, such as T2 dissectioning, adipic saturation and/or a further navigator can be used. Aldo the data of the navigators $N_1$ through $N_4$ accumulated during the coronary angiography can be used in order to improve the prediction of $RR_{pre}$ of step 32.

It is certainly possible to use any diagnostic imaging of position 44, which allows for a depiction of the coronary arteries, at which the sequence of diagnostic imaging should allow for a segmented procedure of recording the MR images, since, because of the short rest period of the diastole, it is not possible to record a complete data record of diagnostic significance.

In summary, the present invention provides a method to predict the position of the diastolic rest period under consideration of the specific connection between the position of the diastolic rest period and the cardiac cycle of the patient under examination while calculating beforehand for each patient to be examined the proportionality factor TF.

To monitor the breathing motion, it is certainly possible to use other methods than MR technologies. Also, the proportionality factor TF can be determined with Doppler ultrasound procedures instead of MR diagnostic imaging Although modifications and changes may be suggested by those skilled in the art, it is the intention of the inventor to embody within the patent warranted hereon all changes and modifications as reasonably and properly come within the scope of his contribution to the art.

I claim as my invention:

1. A computerized method for predicting a diastolic rest period in a cardiac cycle of a subject, comprising the steps of:
   automatically electronically determining a linear relation between the heart rate of the subject and a position of a diastolic rest period in a cardiac cycle of the subject, by determining the diastolic rest period for at least two different heart rates of the subject;
   obtaining a representation of breathing motion of the subject and automatically electronically determining the breathing motion therefrom; and
   automatically electronically predicting a next diastolic rest period using said breathing motion and said linear relation between heart rate and position of the diastolic rest period for the subject.

2. A computerized method as claimed in claim 1 comprising determining said representation of the breathing motion of the subject by determining a representation of movement of the diaphragm of the subject.

3. A computerized method as claimed in claim 2 comprising detecting said movement of the diaphragm of the subject using a sensor that interacts with the subject, said representation of said breathing movement being a signal emitted by said sensor.

4. A computerized method as claimed in claim 3 comprising selecting said sensor from the group of sensors consisting of rate sensors and acceleration sensors.

5. A computerized method as claimed in claim 2 comprising detecting said movement of the diaphragm of the subject by acquiring at least three navigator magnetic resonance images, and automatically electronically identifying at least one of a position, rate and acceleration of the diaphragm of the subject from said at least three magnetic resonance navigator images.

6. A computerized method as claimed in claim 1 comprising determining said linear relation between heart rate and position of the diastolic rest period by acquiring, for each of two different heart rates of the subject, a magnetic resonance image sequence comprising a plurality of magnetic resonance images during one cardiac cycle and, in each image sequence, automatically electronically identifying the position of the diastolic rest period.

7. A computerized method as claimed in claim 6 comprising detecting said movement of the diaphragm of the subject by acquiring at least three navigator magnetic resonance images, and automatically electronically identifying at least one of a position, rate and acceleration of the diaphragm of the subject from said at least three magnetic resonance navigator images.

8. A computerized method as claimed in claim 1 comprising automatically electronically determining said linear relation between heart rate and position of the diastolic rest period for said subject by acquiring an electrocardiogram from the subject at each of two different heart rates, and automatically electronically analyzing said electrocardiogram for each of said two different heart rates to determine a time interval of an R-wave to the position of the diastole, and automatically electronically determining a proportionality factor as a quotient of said time interval and a timed duration between two subsequent R-waves.

9. A computerized method as claimed in claim 8 comprising automatically electronically predicting a time from a last R-wave in said electrocardiogram to a next R-wave in said subject.

10. A computerized method as claimed in claim 9 comprising calculating a duration between said last R-wave and said next diastolic rest period from said predicted duration.

11. A computerized method as claimed in claim 9 comprising predicting said duration using a last two R-waves in said electrocardiogram and said breathing motion.

12. A computerized method as claimed in claim 11 comprising predicting the position of said next diastolic rest period using said proportionality factor and said predicted duration.

13. A computerized method as claimed in claim 1 comprising employing a heart rate of the subject while said subject is resting as one of said at least two different heart rates, and a heart rate that is increased compared to said rest rate as another of said at least two heart rates of the subject.

14. A computerized method as claimed in claim 13 comprising producing said increased heart rate by hyperventilating the subject.

15. A computerized method as claimed in claim 1 comprising the additional step of triggering acquisition of magnetic resonance data for a magnetic resonance image of a coronary artery in said subject, at the predicted next diastolic rest period.

* * * * *